United States Patent
Zheng et al.

(10) Patent No.: US 8,026,488 B2
(45) Date of Patent: Sep. 27, 2011

(54) METHODS FOR POSITIVE EMISSION TOMOGRAPHY (PET) TARGET IMAGE SEGMENTATION

(75) Inventors: Yiran Zheng, Cleveland Heights, OH (US); Barry W. Wessels, Aurora, OH (US)

(73) Assignee: Case Western Reserve University, Cleveland, OH (US)

( * ) Notice: Subject to any disclaimer, the term of this patent is extended or adjusted under 35 U.S.C. 154(b) by 128 days.

(21) Appl. No.: 12/358,750

(22) Filed: Jan. 23, 2009

(65) Prior Publication Data

US 2009/0212225 A1    Aug. 27, 2009

(51) Int. Cl.
*G01T 1/166* (2006.01)

(52) U.S. Cl. .................................. 250/363.03

(58) Field of Classification Search .............. 250/363.03
See application file for complete search history.

(56) References Cited

OTHER PUBLICATIONS

Eric C. Ford et al., "Tumor delineation using PET in head and neck cancers: Threshold contouring and lesion volumes." Med. Phys. 33 (11) (Nov. 2006) p. 4280 <doi:10.1118/1.2361076>.*

Laura Drever et al., "Iterative threshold segmentation for PET target volume delineation." Med. Phys. 34 (4) (Apr. 2007) p. 1253 <doi:10.1118/1.2712043>.*

M. Hatt et al., "A segmentation algorithm for heterogenous tumor automatic delineation in PET." Nuclear Science Symposium Conference Record, 2007, IEEE, vol. 5 (Nov. 2007) p. 3939 <doi:10.1109/NSSMIC.2007.4436980>.*

Erdi, et al.: "*Segmentation of Lung Lesion Volume by Adaptive Positron Emission Tomography Image Thresholding*"; Sixth Conference on Radioimmunodetection and Radioimmunotherapy of Cancer, Supplement to Cancer; American Cancer Society 1997; pp. 2505-2509.

* cited by examiner

*Primary Examiner* — Constantine Hannaher
(74) *Attorney, Agent, or Firm* — Tarolli, Sundheim, Covell & Tummino LLP

(57) ABSTRACT

A method for positive emission tomography (PET) target image segmentation is provided. The method comprises capturing and digitizing image data of a selected target, determining an initial concentration ratio based on an initial source background ratio and an initial volume estimate of the selected target employing a concentration ratio table, determining a desired threshold from the initial concentration ratio and the initial volume estimate employing a threshold table, and determining a final volume estimate of the selected target based on the determined desired threshold.

18 Claims, 5 Drawing Sheets

METHODS FOR POSITIVE EMISSION TOMOGRAPHY (PET) TARGET IMAGE SEGMENTATION

FIELD OF THE INVENTION

The present invention relates to positive emission tomography (PET), and particularly relates to methods for PET target image segmentation.

BACKGROUND

Positron emission tomography (PET) using glucose analog [$^{18}$F]2-fluoro-D-2-deoxyglucose (FDG) has been developed essentially as a diagnostic tool for neoplasms. Recently, FDG-PET has been used for staging, treatment response, restaging after therapy and prognosis for lymphoma, lung cancer, head and neck tumors, thyroid carcinoma, breast cancer, and many other malignances. Besides its use as a diagnostic tool in oncology, FDG-PET is increasingly used in target volume definition as a planning tool for radiotherapy. The role of FDG-PET in radiation therapy treatment planning has been investigated for several malignancies including lung, head and neck, brain, cervix and other tumor sites. FDG-PET imaging has had a great impact on the gross tumor volume (GTV) definition, especially for lung cancer. Unfortunately, in recent literatures, there is no general agreement about a uniformly applicable method for accurate target volume delineation.

The accuracy of GTV definition is essential in conformal radiation therapy such as intensity modulated radiation therapy (IMRT). Conventionally, GTV was based on volume data derived from CT scanning. However, CT has relatively low contrast for soft tissue which makes it difficult to differentiate the malignancy when the tumor has similar electron density with normal tissue. Previous investigation suggests that FDG-PET has the potential to provide more accurate GTV definition and reduce inter-observer variability. The research shows FDG-PET based GTV definition is superior to those by CT alone for a moving target. However, comparing to CT or MRI images, FDG-PET images have low spatial resolution, high partial volume effect and insufficient anatomical details which result in difficulty to define the exact border of tumor. More attention and efforts are considered necessary to incorporate PET functional imaging information into radiation therapy treatment planning.

Currently, thresholding segmentation is the most widely used automatic method for PET target delineation in research and clinical application although other techniques are also under investigation. A relatively simple thresholding method using fixed threshold of 40% of maximal image intensity or standardized uptake value (SUV) of 2.5 as a cut off factor is still employed in clinical application. Many recent investigations indicate that the fixed thresholding or absolute value thresholding is of limited accuracy, especially for targets with small volume or low contrast. The optimal threshold which can best define the actual target volume depends on source/background image intensity ratio (S/B ratio) and target volume.

Accordingly, an adaptive thresholding method was developed using a computer tomography (CT) volume as the initial estimate of target volume. In this method, a family of exponential threshold-volume curves for different S/B ratios was obtained from fitting data of an initial sphere phantom study. Depending on measured target S/B ratio, the given CT volume was applied to the corresponding curve to yield the desired threshold for target delineation. Based on the same hypothesis, an iterative method was developed recently. Instead of using CT volume as a prior knowledge, the threshold deriving from fitted curves and thresholding segmentation procedures were performed iteratively until the yielded threshold would not change. Another local contrast based method employed similar iterative technique slice-by-slice to obtain the desired threshold for each slice instead of one global threshold for the whole volume. The adaptive thresholding method had good performance if given the target CT volume which is not always available in clinic. The iterative methods do not need the CT volume as initial estimate of target volume. However the convergence of the iterative procedure is questionable when applied to a target volume smaller than 4 mL. Moreover, these methods confuse the S/B ratio with physical FDG concentration ratio of target and background. Unlike the above techniques, Black's mean SUV method employed a linear relationship between threshold SUV and mean target SUV iteratively to yield desired threshold SUV. Because the SUV are machine-specific and patient-specific values, this linear relationship needs to be modified to accommodate different scanners.

SUMMARY OF THE INVENTION

The present invention relates to a methods for positive emission tomography (PET) target image segmentation, In one embodiment, a method is provided that comprises capturing and digitizing image data of a selected target, determining an initial concentration ratio based on an initial source background ratio and an initial volume estimate of the selected target employing a concentration ratio table, and determining a desired threshold from the initial concentration ratio and the initial volume estimate employing a threshold table. A final volume estimate of the selected target is determined based on the determined desired threshold.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

The present invention relates to methods for PET target image segmentation. The methods employ a concentration ratio lookup table and a threshold lookup table to derive a desired threshold value that determines which portion of an image represents a selected target image and which portion of the image represents background. For example, normalized pixel intensity values above or equal the desired threshold can be determined to be part of the selected target image and normalized pixel intensity values below the desired threshold can be determined to be part of the background. An initial estimate of target volume and a source background ratio based on the initial estimate of target volume are employed to determine a concentration ratio provided in the concentration ratio table. The estimates of target volume and concentration ratio are employed to determine a desired threshold value provided in the threshold lookup table. These estimated are not required to be absolutely accurate, but as long as the estimates fall into a correct category, the threshold derived from the threshold lookup table results in acceptable target delineation.

Figure 1:
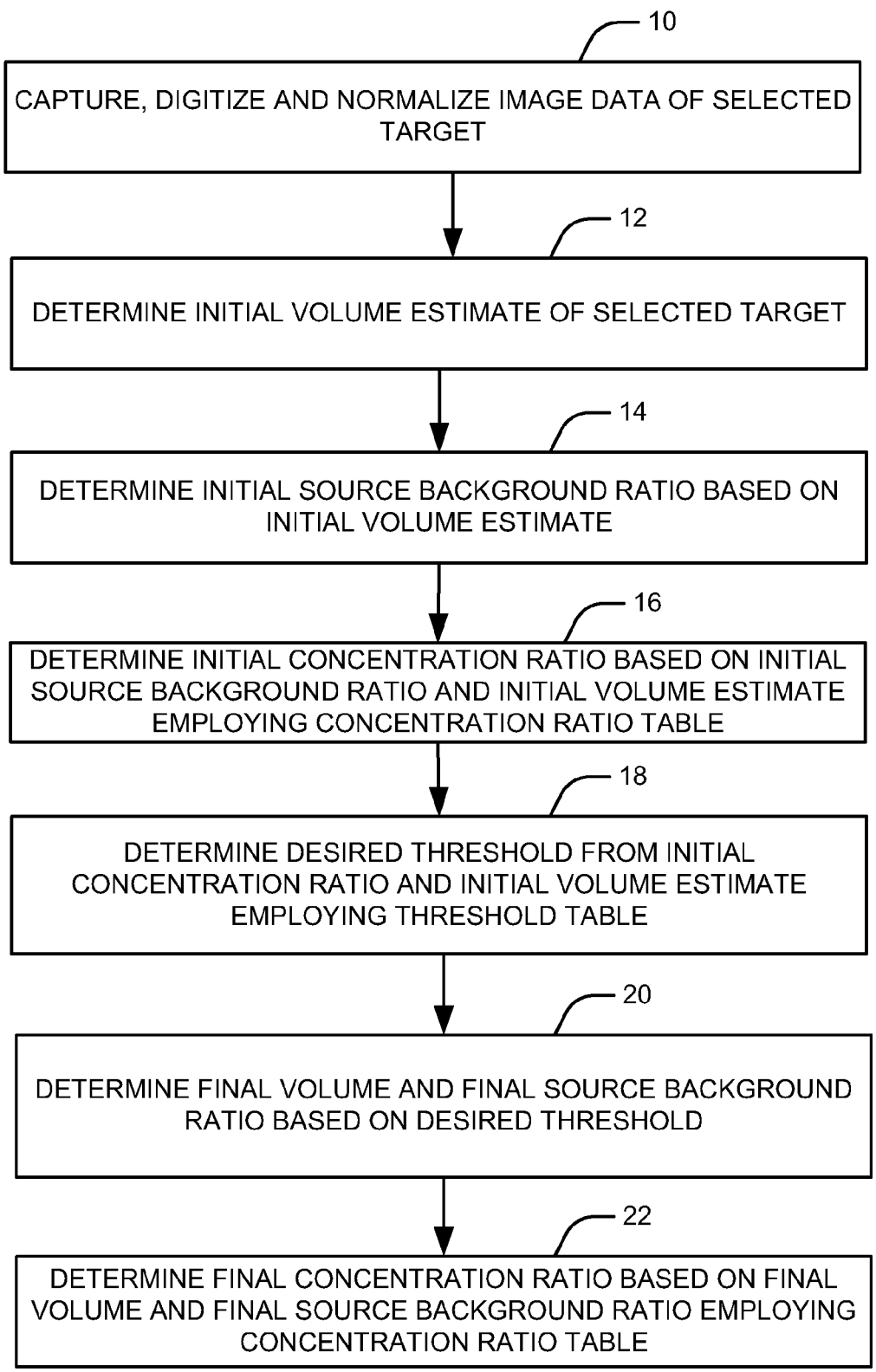
FIG. 1 illustrates a flow diagram of a methodology for PET target image segmentation in accordance with an aspect of the present invention.
Figure 2:
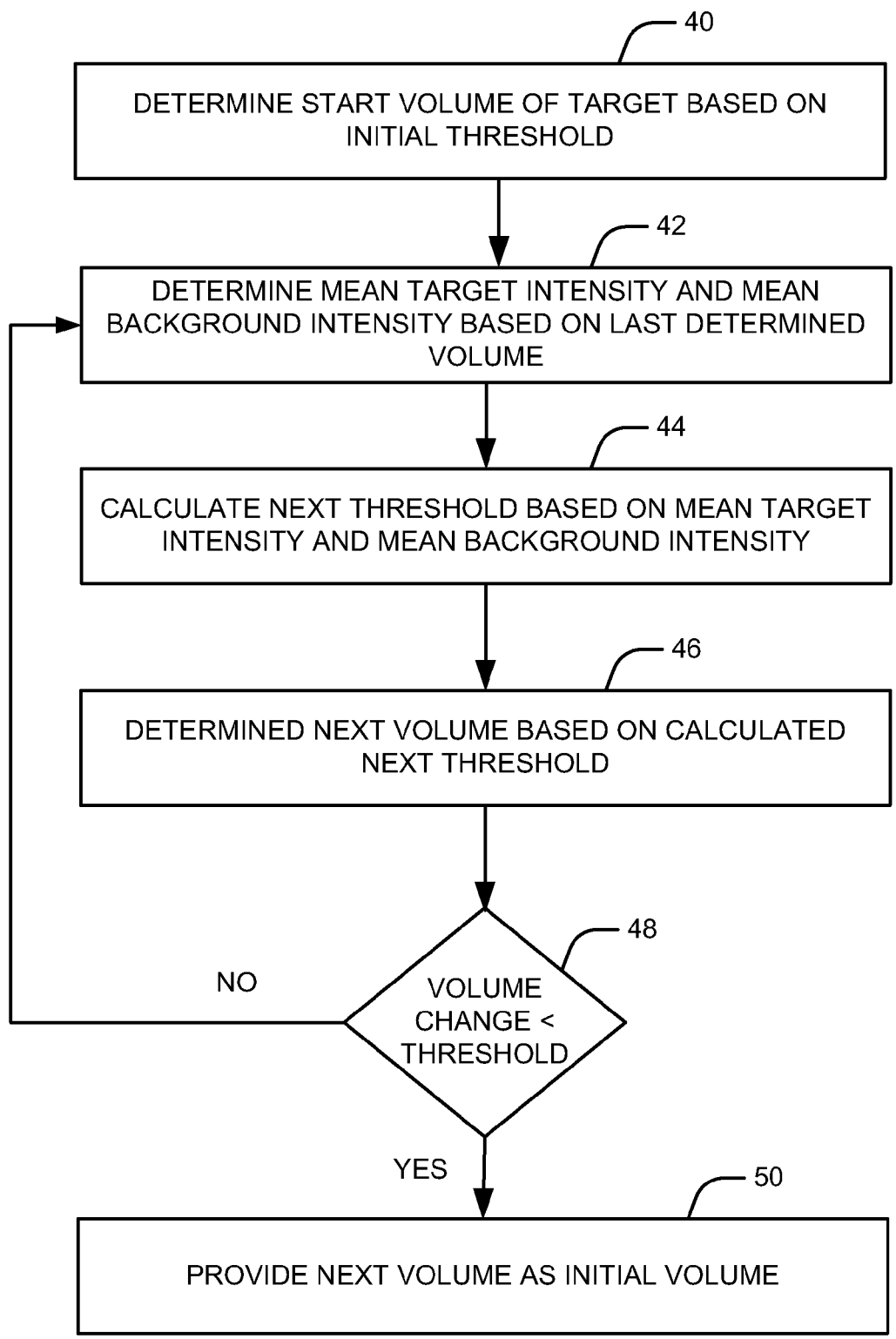
FIG. 2 illustrates a mean intensity threshold methodology for determining an initial volume estimate of a selected target with a PET target image in accordance with an aspect of the present invention.

FIG. 1 illustrates a methodology for PET target image segmentation in accordance with an aspect of the present invention. At 10, an image data of a selected target (e.g., a tumor) is captured, digitized and normalized. The image data can be normalized by dividing each pixel value by a maximum pixel value. At 12, an initial volume estimate of the selected target image is obtained. The initial volume estimate can obtained employing a CT image of the selected target. Alternatively, an initial volume estimate of the selected target image can be provided by employing a mean intensity threshold method as illustrated in FIG. 2. At 14, an initial source background ratio is determined based on the initial volume estimate of the selected target. The initial source background ratio is determined based on a maximum intensity value of the selected target divided by the mean intensity value of the background pixels (i.e., non-selected background portion of the image data). At 16, an initial concentration ratio is determined based on the initial source background ratio and the initial volume estimate employing the following Concentration ratio table I below:

TABLE 1

Concentration ratio recovery

| | C | | | |
|---|---|---|---|---|
| | SB >= 6.5 | 5 <= SB < 6.5 | 3.5 <= SB < 5 | 2 <= SB < 3.5 |
| V > 4 cc | 1.60 * SB | 1.40 * SB | 1.33 * SB | 1.15 * SB |
| V <= 4 cc | | C = 0.6 * (7 − V) * SB | | 0.4 * (7 − V) * SB | where V is the volume estimate, SB is the source background ratio and C is the concentration ratio. The methodology then proceeds to 18.

At 18, a desired threshold is determined from the initial concentration ratio and initial volume estimate employing threshold table II below:

TABLE 2

Threshold categorized by initial volume estimate and concentration ratio

| | Threshold | | |
|---|---|---|---|
| | C < 4:1 | 4:1 <= C < 10:1 | C >= 10:1 |
| V < 2.5 cc | 73.6% | 59.8% | 53.1% |
| V >= 2.5 CC | 54.5% | 44.9% | 41.2% | where V is the initial volume estimate, C is the concentration ratio determined in Table I and the Threshold is the desired threshold value to be employed in determining a final volume estimate. At 20, a final volume estimate and a final source background ratio is determined based on the desired threshold value determined in Table II. At 22, a final concentration ratio is determined based on the final volume estimate and a final source background ratio employing the concentration ratio table I.

FIG. 2 illustrates a mean intensity threshold methodology for determining an initial volume estimate of a selected target with a PET target image in accordance with an aspect of the present invention. At 40, a start volume is determined based on an initial threshold value. For a fixed threshold method, a threshold value of 36%~40% has been suggested in the literature as being appropriate for all volumes greater than 4 mL. Therefore, a 40% threshold can be employed as an initial threshold value. At 42, a mean target intensity and a mean background intensity are determined based on the start volume. The mean target intensity is the average of all the pixel intensity values that are determined to the part of the target and the mean background intensity is the average of all of the pixel intensity values that are determined to be part of the background. At 44, a next threshold value is determined based on the mean target intensity and the mean background intensity by evaluating the following equation;

$$\text{Next Threshold}=0.502*MTI+0.57*MBI \qquad \text{EQ. 1}$$

where MTI is the Mean Target Intensity and MBI is the Mean Background Intensity. The methodology then proceeds to 46.

At 46, the next volume estimate is determined based on the next threshold value. At 48 the next volume estimate is compared to the previously determined volume estimate to determine if the volume change is less than a predetermined volume change threshold (e.g., 0.1 cc). If the volume change is not less than the predetermined volume change threshold (NO), then the methodology returns to repeat 42, 44, 46 and 48 to determine a new next volume based on a newly calculated next threshold until the volume change is less than the predetermined volume change threshold. If the volume change is less than the predetermined volume change threshold (YES), then the methodology proceeds to 50. At 50, the methodology provides the next volume as the initial volume to 14 of FIG. 1.

FIGS. 3-6 and the following description provide details on the determination of the Concentration Ratio TABLE I and the Threshold Value Table II. A series of phantom studies were conducted to investigate and quantify the relationship between optimal threshold, target volume and target-background concentration ratio. Eight spheres with volume ranging from 1 mL to 95 mL (1, 2, 5.7, 8.3, 11.6, 18.9, 19.3 and 95 mL) were injected a uniform concentration of [$^{18}$F]2-fluoro-D-2-deoxyglucose (FDG) and imaged in a Jaszczak phantom. Each sphere was held by a rod within this elliptical Jaszczak phantom which has total volume of 9500 mL imitating the size and shape of human thorax. To emulate the typical background activity in patient studies, 0.145 µCi/mL FDG was filled in the Jaszczak phantom as background activity. The target-to-background FDG concentration ratio was varied from 3:1 to 12:1 in different scanning sessions. Although the wall of each hollow sphere contained no FDG activity, the wall thickness was approximately 1 mm which was much smaller than PET image resolution and could be neglected in the reconstructed images.

The spheres were dispersed within the phantom at least 4 cm of space between sphere edges. The sphere volumes were measured by an infusion syringe pump (Graseby 3400, Graseby Medical Ltd.) with precision of ±0.1 mL and the FDG concentrations were monitored with a dose calibrator (Deluxe Isotope Calibrator II, Victoreen Inc.). The well-defined sphere geometry and concentration ratio provided accurate optimal threshold estimation for wide range of target volume and target-to-background concentration ratio. The phantom was scanned with an Allegro PET scanner (Philips Medical Systems) using high-resolution pixilated GSO (gadolinium orthosilicate) detectors. The Allegro scanner has 82 cm diameter detector ring and an axial field of view (FOV) of 18 cm. The point source spatial resolution near the center was ~5.5 mm and 5.2 mm in the transverse and axial direction respectively (wide profile, NEMA NU 2-2001). The imaging procedure was analogous to clinical application of lung cancer PET scanning. The clinical protocol for lung scanning was used with 2 beds and 3 min/bed emission scanning in full 3D mode.

After scanning, 3D row-action maximum-likelihood algorithm (3D-RAMLA) reconstruction was performed with decay correction, background subtraction and attenuation correction. The reconstructed PET image resolution was 4×4 mm$^2$ with a slice thickness of 4 mm, Reconstructed PET images were analyzed by a user developed Matlab program (The MathWorks, Inc., version 7.4 release 2007a). For each sphere with different volume and concentration ratio, an optimal threshold was determined when the difference between the calculated target volume and the actual physical volume was negligible using a binary search program. Instead of utilizing machine specific curve fitting parameters, a simple six group threshold lookup table (see Table II) comprised only of target volumes and concentration ratios were used. To employ this threshold lookup table, the target volume and the concentration ratio were estimated before derive the desired threshold. As previously described, the entire workflow of the PET image segmentation method is illustrated in FIG. 1.

A mean intensity segmentation method as illustrated in FIG. 2 was used to derive the initial estimate of the target volume. Unbiased linear relationship among optimal threshold intensity, mean target intensity and mean background intensity was derived by fitting sphere phantom data. The threshold intensity determined by EQ. 1 was a particular absolute value of image intensity which can be normalized by maximum intensity. The first segmentation was acquired using 40% threshold value. The first mean target intensity and mean background intensity were measured to calculate the new threshold intensity according to this linear relationship. The new segmentation, new mean target and background intensity were determined based on the new threshold intensity and was used to calculate the next threshold intensity. By repeating this procedure, the threshold converged to a fixed value eventually after no more than 15 iterations. The convergent threshold was used to obtain the initial estimate of target volume. Although this initial estimate led to considerable error for target delineation especially for small size target, it provided satisfactory input data to use.

The output of mean intensity segmentation also included source/background (S/B) ratio which was the ratio of the maximum image intensity within the target to the average background intensity excluding target. Based on the initial estimate of target volume and measured S/B ratio, the FDG activity concentration ratio was recovered by another lookup table (see Table I). The recovered concentration ratio combined with the initial estimate of target volume provided enough information to derive the desired threshold from the threshold lookup table (see Table II). As the last step, the thresholding segmentation delineated the target for each individual slice and the target volume was calculated afterwards.

Figure 3:
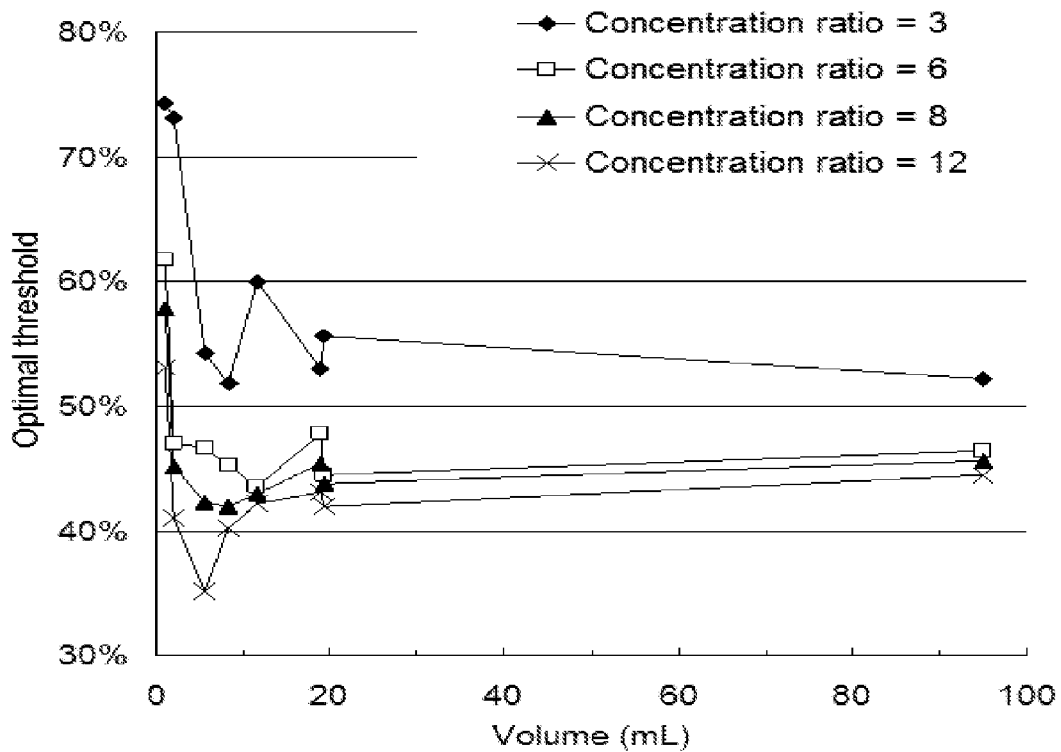
FIG. 3 illustrates a graph of optimal thresholds for each sphere volume and concentration ratio combination in accordance with an aspect of the invention.

The optimal thresholds for each sphere volume and concentration ratio combination are plotted in FIG. 3. Each optimal threshold depended on sphere volume and concentration ratio. However, no simple curve could model the data. To summarize the relationship among optimal threshold, target volume and concentration ratio, the lookup threshold table II was generated. Based on the similarity with neighboring data point, the optimal thresholds were categorized into six groups as illustrated in the threshold lookup table plot of FIG. 4. The average of optimal thresholds of each group was used as the desired threshold for the corresponding target volume and concentration ratio of the group.

Figure 4:
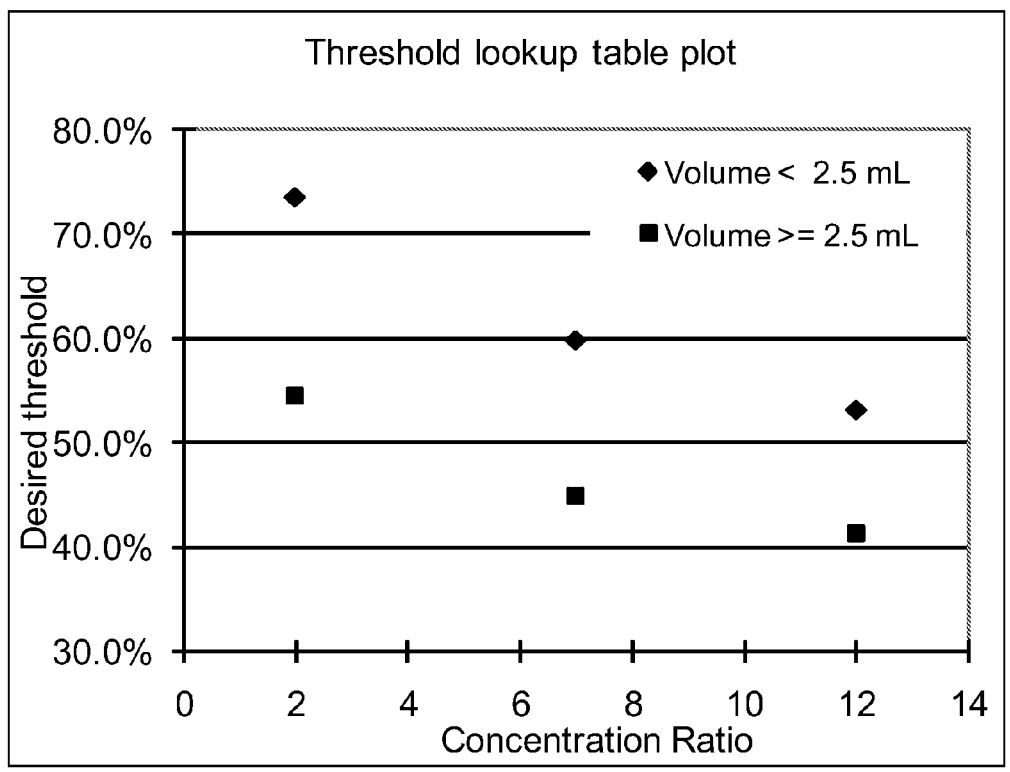
FIG. 4 illustrates a threshold lookup table plot of desired threshold versus concentration ratio in accordance with an aspect of the invention.

Given the initial estimate of target volume and concentration ratio which is within the range of the corresponding group, the threshold from FIG. 4 and table II can yield the target delineation within acceptable deviation from actual volume. However, the target volume and concentration ratio both cannot be obtained from PET image directly. The target volume was a primary variable under investigation. The physical concentration ratio to be recovered is related to the S/B ratio along with the target volume.

Figure 5:
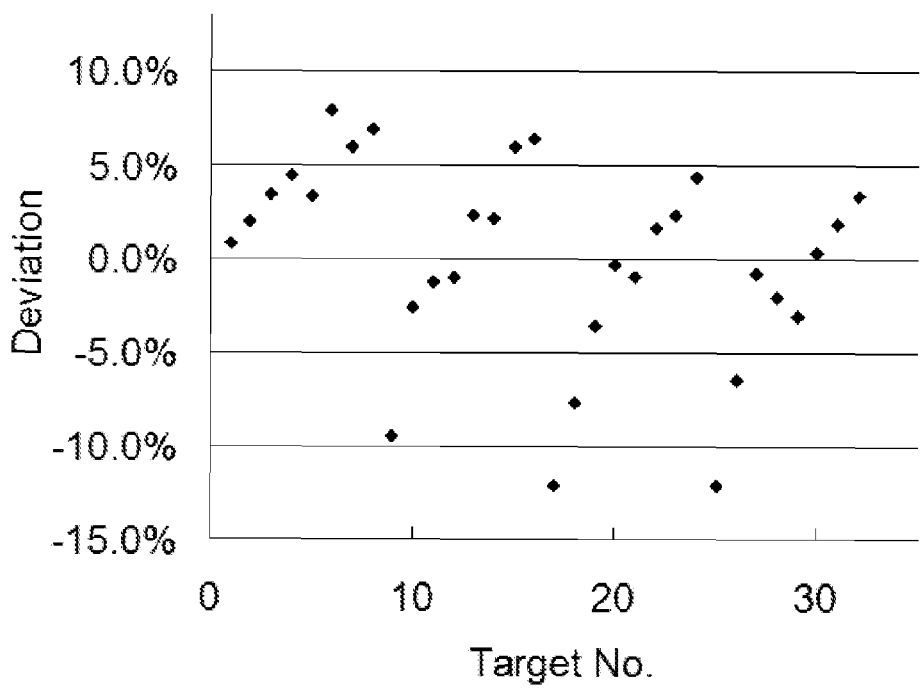
FIG. 5 illustrates a graph of error distribution versus target number in accordance with an aspect of the invention.
Figure 6:
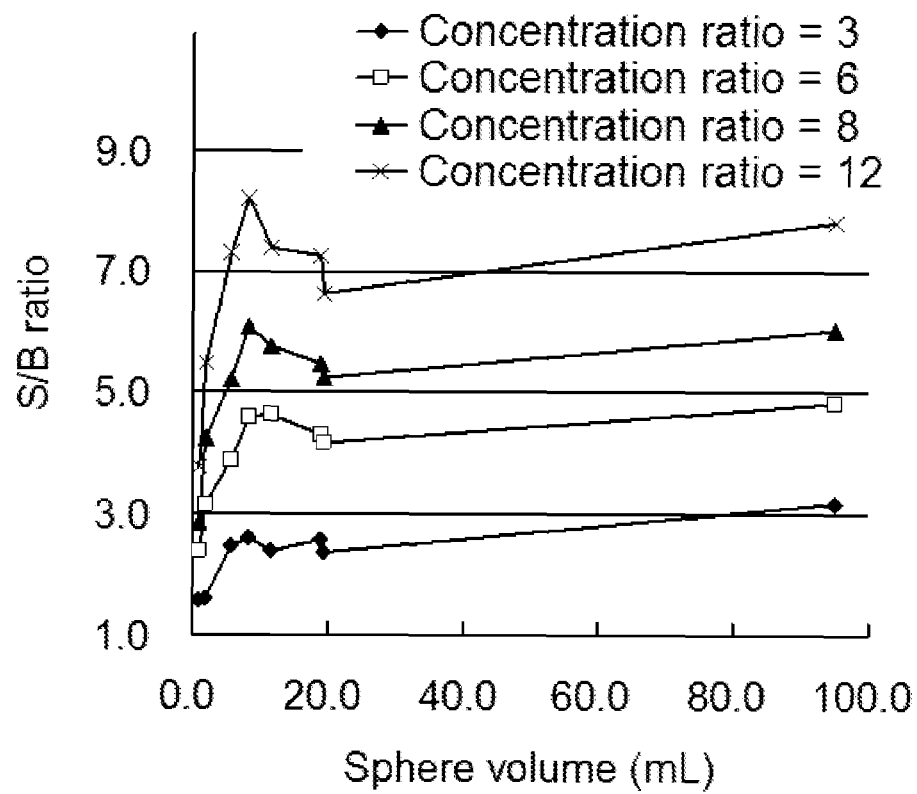
FIG. 6 illustrates a graph of S/B ratio versus sphere volume to determine concentration ratio in accordance with an aspect of the invention.

The phantom data analysis showed that the optimal threshold had a linear relationship with the mean target intensity and mean background intensity. Multiple linear regression analysis established a relationship between the mean target intensity and mean background intensity, and the threshold in absolute intensity (See Eq. 1). All the variables expressed in intensity units were normalized to a percentage of target maximum intensity. The correlation coefficient ($r^2$) of linear regression curve fitting was 0.968. The error distribution of the multiple linear regression is illustrated in FIG. 5. All the errors were within the range of −12.1% to 7.9% with standard deviation of 5.2%. Although this error of threshold estimation can induce improper volume segmentation with over 100% volume estimation error, especially for small spheres, the results were appropriate as an initial volume estimate. According to the error distribution, there was still a tendency that the thresholds for small volumes were underestimated and the thresholds for large volumes were overestimated. This tendency could not be eliminated by a linear regression model.

The output of mean intensity segmentation also included S/B ratio. From the sphere phantom data, it was determined that the S/B ratio depended both on concentration ratio and sphere volume, especially for a small size sphere. However, according to the relationship shown in FIG. 6, the concentration ratio could be recovered from the initial estimate of target volume and estimated S/B ratio. Similarly, because no simple curve can fit all the data points easily, another lookup table (Table I) was constructed. With the initial estimate of target volume and measured S/B ratio, the concentration ratio was recovered based on this table (Table I). The recovered concentration ratio combined with the initial estimate of target volume provided enough information to derive the desired threshold from threshold lookup table (Table I) to delineate the target.

Figure 7:
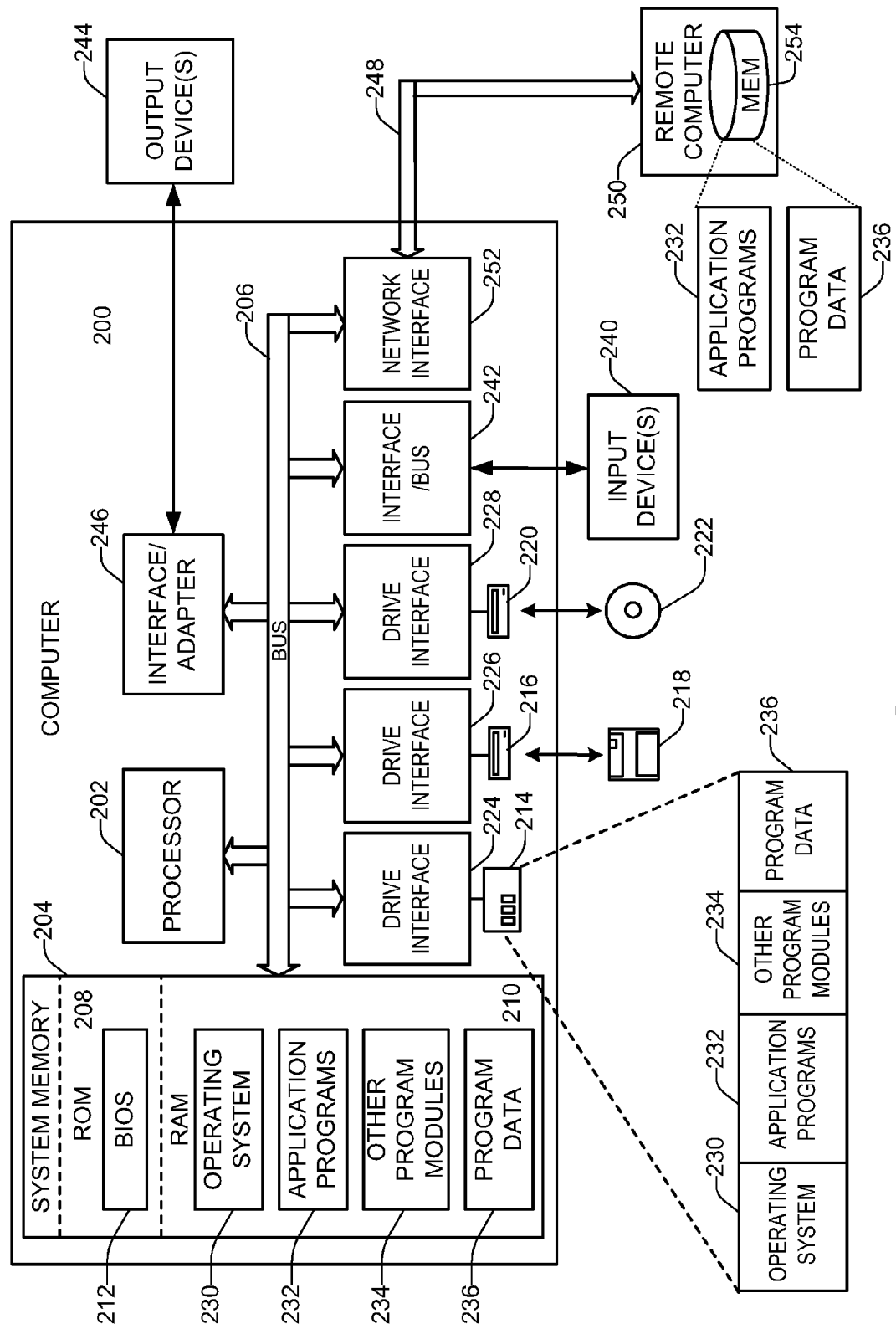
FIG. 7 illustrates a computer system that can be employed to implement systems and methods in accordance with one or more aspects of the invention.

FIG. 7 illustrates a computer system 200 that can be employed to implement systems and methods described herein, such as based on computer executable instructions running on the computer system. The computer system 200 can be implemented on one or more general purpose networked computer systems, embedded computer systems, routers, switches, server devices, client devices, various intermediate devices/nodes and/or stand alone computer systems. Additionally, the computer system 200 can be implemented as part of the computer-aided engineering (CAE) tool running computer executable instructions to perform a method as described herein.

The computer system 200 includes a processor 202 and a system memory 204. A system bus 206 couples various system components, including the system memory 204 to the processor 202. Dual microprocessors and other multi-processor architectures can also be utilized as the processor 202. The system bus 206 can be implemented as any of several types of bus structures, including a memory bus or memory controller, a peripheral bus, and a local bus using any of a variety of bus architectures. The system memory 204 includes read only memory (ROM) 208 and random access memory (RAM) 210. A basic input/output system (BIOS) 212 can reside in the ROM 208, generally containing the basic routines that help to transfer information between elements within the computer system 200, such as a reset or power-up.

The computer system 200 can include a hard disk drive 214, a magnetic disk drive 216, e.g., to read from or write to a removable disk 218, and an optical disk drive 220, e.g., for reading a CD-ROM or DVD disk 222 or to read from or write to other optical media. The hard disk drive 214, magnetic disk drive 216, and optical disk drive 220 are connected to the system bus 206 by a hard disk drive interface 224, a magnetic disk drive interface 226, and an optical drive interface 228, respectively. The drives and their associated computer-readable media provide nonvolatile storage of data, data structures, and computer-executable instructions for the computer system 200. Although the description of computer-readable media above refers to a hard disk, a removable magnetic disk and a CD, other types of media which are readable by a computer, may also be used. For example, computer executable instructions for implementing systems and methods described herein may also be stored in magnetic cassettes, flash memory cards, digital video disks and the like.

A number of program modules may also be stored in one or more of the drives as well as in the RAM 210, including an operating system 230, one or more application programs 232, other program modules 234, and program data 236. The one or more application programs can include the methods for PET target image segmentation as described in FIGS. 1-6.

A user may enter commands and information into the computer system 200 through user input device 240, such as a keyboard, a pointing device (e.g., a mouse). Other input devices may include a microphone, a joystick, a game pad, a scanner, a touch screen, or the like. These and other input devices are often connected to the processor 202 through a corresponding interface or bus 242 that is coupled to the system bus 206. Such input devices can alternatively be connected to the system bus 206 by other interfaces, such as a parallel port, a serial port or a universal serial bus (USB). One or more output device(s) 244, such as a visual display device or printer, can also be connected to the system bus 206 via an interface or adapter 246. The computer system 200 may operate in a networked environment using logical connections 248 to one or more remote computers 250. The remote computer 250 may be a workstation, a computer system, a router, a peer device or other common network node, and typically includes many or all of the elements described relative to the computer system 200. The logical connections 248 can include a local area network (LAN) and a wide area network (WAN).

When used in a LAN networking environment, the computer system 200 can be connected to a local network through a network interface 252. When used in a WAN networking environment, the computer system 200 can include a modem (not shown), or can be connected to a communications server via a LAN. In a networked environment, application programs 232 and program data 236 depicted relative to the computer system 200, or portions thereof, may be stored in memory 254 of the remote computer 250.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

Having described the invention the following is claimed:

1. A method for positive emission tomography (PET) target image segmentation, the method comprising:
   receiving, by a computer system, captured and digitized image data of a selected target;
   determining, by the computer system, an initial volume estimate of the selected target based on the image data of the selected target;
   determining, by the computer system, an initial concentration ratio based on an initial source background ratio and the initial volume estimate of the selected target employing a concentration ratio table;
   determining, by the computer system, a desired threshold from the initial concentration ratio and the initial volume estimate employing a threshold table; and
   determining, by the computer system, a final volume estimate of the selected target based on the determined desired threshold.

2. The method of claim 1, further comprising determining, by the computer system, the initial volume estimate based on a mean intensity threshold method.

3. The method of claim 2, further comprising determining, by the computer system, the initial source background ratio based on the initial volume estimate.

4. The method of claim 1, further comprising determining, by the computer system, the initial volume estimate based on a computer tomography (CT) image of the selected target.

5. The method of claim 1, determining, by the computer system, a final concentration ratio based on the final volume estimate and a final source background ratio employing the concentration ratio table.

6. The method of claim 5, further comprising determining, by the computer system, the final source background ratio based on the final volume estimate.

7. A non-transitory computer readable medium having computer executable instructions for performing a method for positive emission tomography (PET) target image segmentation, the method comprising:
   receiving captured and digitized image data of a selected target;
   determining an initial volume estimate of the selected target based on the image data of the selected target;
   determining an initial concentration ratio based on an initial source background ratio and the initial volume estimate of the selected target employing a concentration ratio table;
   determining a desired threshold from the initial concentration ratio and the initial volume estimate employing a threshold table; and
   determining a final volume estimate of the selected target based on the determined desired threshold.

8. The non-transitory computer readable medium of claim 7, wherein the method further comprises determining the initial volume estimate based on a mean intensity threshold method.

9. The non-transitory computer readable medium of claim 8, wherein the method further comprises determining the initial source background ratio based on the initial volume estimate.

10. The non-transitory computer readable medium of claim 7, wherein the method further comprises determining the initial volume estimate based on a computer tomography (CT) image of the selected target.

11. The non-transitory computer readable medium of claim 7, wherein the method further comprises determining a final concentration ratio based on the final volume estimate and a final source background ratio employing the concentration ratio table.

12. The non-transitory computer readable medium of claim 11, wherein the method further comprises determining the final source background ratio based on the final volume estimate.

13. A computer system comprising:
   a memory for storing computer executable instructions; and
   a processor for accessing the memory and executing the computer executable instructions, the computer executable instructions being configured to perform a method for positive emission tomography (PET) target image segmentation, the method comprising:
      receiving captured and digitized image data of a selected target;
      determining an initial volume estimate of the selected target based on the image data of the selected target;
      determining an initial concentration ratio based on an initial source background ratio and the initial volume estimate of the selected target employing a concentration ratio table;
      determining a desired threshold from the initial concentration ratio and the initial volume estimate employing a threshold table; and
      determining a final volume estimate of the selected target based on the determined desired threshold.

14. The computer system of claim 13, wherein the method further comprises determining the initial volume estimate based on a mean intensity threshold method.

15. The computer system of claim 14, wherein the method further comprises determining the initial source background ratio based on the initial volume estimate.

16. The computer system of claim 13, wherein the method further comprises determining the initial volume estimate based on a computer tomography (CT) image of the selected target.

17. The computer system of claim 13, wherein the method further comprises determining a final concentration ratio based on the final volume estimate and a final source background ratio employing the concentration ratio table.

18. The computer system of claim 17, wherein the method further comprises determining the final source background ratio based on the final volume estimate.

* * * * *